(12) United States Patent
Chin et al.

(10) Patent No.: US 10,422,770 B2
(45) Date of Patent: Sep. 24, 2019

(54) DETECTION OF VIABLE PATHOGENS IN ANALYTE USING CULTURE CHAMBER WITH MAGNETOSTRICTIVE SENSORS

(71) Applicant: Auburn University, Auburn, AL (US)

(72) Inventors: Bryan A. Chin, Auburn, AL (US); Shin Horikawa, Auburn, AL (US); Zhongyang Cheng, Auburn, AL (US)

(73) Assignee: Auburn University, Auburn, AL (US)

( * ) Notice: Subject to any disclaimer, the term of this patent is extended or adjusted under 35 U.S.C. 154(b) by 166 days.

(21) Appl. No.: 15/631,150

(22) Filed: Jun. 23, 2017

(65) Prior Publication Data
US 2017/0370882 A1 Dec. 28, 2017

Related U.S. Application Data

(60) Provisional application No. 62/353,931, filed on Jun. 23, 2016.

(51) Int. Cl.
*G01N 27/74* (2006.01)
*G01N 27/00* (2006.01)
(Continued)

(52) U.S. Cl.
CPC .............. *G01N 27/74* (2013.01); *G01N 29/02* (2013.01); *G01N 29/036* (2013.01); *G01N 29/222* (2013.01); *G01N 29/2412* (2013.01); *G01N 33/53* (2013.01); *G01N 33/5434* (2013.01); *G01N 33/54326* (2013.01);
(Continued)

(58) Field of Classification Search
CPC ..... G01N 2291/014; G01N 2291/0255; G01N 2291/0256; G01N 2291/106; G01N 27/00; G01N 27/74; G01N 29/02; G01N 29/036; G01N 29/222; G01N 29/2412;
(Continued)

(56) References Cited

U.S. PATENT DOCUMENTS 7,138,238 B2   11/2006   Vodyanoy et al.
7,267,993 B2   9/2007    Pentrenko et al.
(Continued)

OTHER PUBLICATIONS

Shen et al. Materials Resource Soc. Symp. Proc., vol. 1253, 2010, pp. 1-7.*
(Continued)

*Primary Examiner* — Maureen Wallenhorst
(74) *Attorney, Agent, or Firm* — Barnes & Thornburg LLP

(57) ABSTRACT

In at least one illustrative embodiment, a system may include a basin that includes an index plate positioned at a bottom of the basin. The basin is configured to receive a liquid analyte, such as a liquid food product or a nutrient broth. The index plate includes an array of multiple wells. Each well opens into an interior of the basin and is sized to receive a magnetostrictive sensor in a predetermined orientation. One or more sensor coils is positionable beneath each well. The basin may be filled with liquid analyte and magnetostrictive sensors may be positioned in the wells. The liquid analyte may be allowed to incubate at a controlled temperature. A controller may position a sensor coil beneath a well, apply a varying magnetic field to a magnetostrictive sensor in the well, and detect a frequency response of the magnetostrictive sensor. Other embodiments are described and claimed.

10 Claims, 5 Drawing Sheets

(51) Int. Cl.
*G01N 29/02* (2006.01)
*G01N 33/53* (2006.01)
*G01N 33/543* (2006.01)
*G01N 33/569* (2006.01)
*G01N 29/036* (2006.01)
*G01N 29/22* (2006.01)
*G01N 29/24* (2006.01)

(52) U.S. Cl.
CPC ..... *G01N 33/54373* (2013.01); *G01N 33/569* (2013.01); *G01N 27/00* (2013.01); *G01N 2291/014* (2013.01); *G01N 2291/0255* (2013.01); *G01N 2291/0256* (2013.01); *G01N 2291/106* (2013.01)

(58) Field of Classification Search
CPC ............. G01N 33/53; G01N 33/54326; G01N 33/5434; G01N 33/54373; G01N 33/569
USPC ...... 436/20, 22, 23, 149, 150, 151; 435/4, 5, 435/29, 34, 39, 40; 422/82.01, 82.02
See application file for complete search history.

(56) References Cited

U.S. PATENT DOCUMENTS

| | | | |
|---|---|---|---|
| 7,670,765 B2 | 3/2010 | Petrenko et al. | |
| 7,759,134 B2 | 7/2010 | Chin et al. | |
| 2005/0181508 A1* | 8/2005 | Fredriksson | C12N 13/00 435/459 |
| 2012/0280682 A1* | 11/2012 | Cheng | G01N 29/2412 324/301 |
| 2014/0120524 A1 | 5/2014 | Chin et al. | |

OTHER PUBLICATIONS

Lakshmanan et al. Sensors and Actuators B, vol. 126, 2007, pp. 544-550.*
Li et al. Proc. of SPIE, vol. 9488, 2015, pp. 948803-1-948803-10.*
Li et al. Proc. of SPIE, vol. 7676, 2010, pp. 76760N-1-76760N-8.*
Horikawa et al. Proc. of SPIE, vol. 8369, 2012, pp. 83690N-1-83690N-7.*

* cited by examiner

DETECTION OF VIABLE PATHOGENS IN ANALYTE USING CULTURE CHAMBER WITH MAGNETOSTRICTIVE SENSORS

CROSS-REFERENCE TO RELATED APPLICATION

This application claims priority to U.S. Provisional Application Ser. No. 62/353,931, filed Jun. 23, 2016, the entire disclosure of which is hereby incorporated by reference.

BACKGROUND

Foodborne illnesses are primarily caused by food contaminated with pathogenic microorganisms in the field or during food processing under insanitary conditions. Hence, surveillance of bacterial contamination of fresh produce through the food supply chain is of great importance to the food industry. However, such surveillance is a challenge since the food supply chain is a lengthy trail with many opportunities to cause food contamination. Food products may be cleaned at the harvesting site, transported to a warehouse, re-cleaned, and repackaged several times before reaching retail outlets.

Typical microbiological methods for pathogen detection, such as colony counting, immunoassay, and polymerase chain reaction (PCR), offer very high sensitivities. However, they require pre-analytical sample preparation, which generally includes sample collecting, separating target pathogen cells from food, increasing cell concentration, and achieving analysis volume from bulk samples before detection. These processes are time consuming, resulting in delays in obtaining the screening results. Also, only small samples (for example, 1 mL samples) may be evaluated for pathogens. More importantly, food samples have to be delivered to laboratories for culture preparation and analysis. Label-free biosensors are available in today's market. However, they also require sample preparation prior to the actual testing (i.e. sampling from fresh produce, filtration and purification of the collected samples, and injection of the filtered/purified samples into a flow system where a biosensor resides). Due to the complexity of these test procedures and the requirements of expensive equipment and highly trained personnel, current food safety controls mainly rely on control of worker/environment hygiene in the food processing industry, rather than the direct pathogen detection.

Free-standing phage-based magnetoelastic biosensors have been investigated as a label-free wireless biosensor system for real-time pathogen detection. The magnetoelastic biosensor is typically composed of a magnetoelastic resonator that is coated with a bio-molecular recognition element that binds specifically with a target pathogen. Once the biosensor comes into contact with the target pathogen, binding occurs, causing an increase in the mass of the resonator resulting in a decrease in the resonant frequency of the sensor (as well as other characteristic frequencies of the sensor).

SUMMARY

According to one aspect, a system for contaminant detection may include a basin and a sensor coil. The basin includes an index plate positioned at a bottom of the basin. The index plate includes an array of wells. Each well of the array of wells opens into an interior of the basin and is sized to receive a magnetostrictive sensor in a predetermined orientation. The basin is configured to receive a liquid analyte. The sensor coil is positionable beneath each well of the array of wells.

In some embodiments, the basin may include a wall coupled to the index plate. The wall surrounds the array of wells. In some embodiments, the index plate may comprise polyethylene terephthalate glycol-modified and the wall may comprise polydimethylsiloxane. In some embodiments, the system may further include a transparent cover coupled to a top of the basin and an infrared heating element configured to heat the interior of the basin.

In some embodiments, the basin is translatable relative to the sensor coil. In some embodiments, the system may further include an array of sensor coils positioned beneath the index plate. The array of sensor coils includes the sensor coil, and each sensor coil of the array of sensor coils may be positioned beneath a well of the array of wells.

In some embodiments, each well may have a length dimension that is between 1.00001% and 1.2% percent larger than a length dimension of the magnetostrictive sensor. In some embodiments, each well may have a depth dimension that is between 1 to 10,000 times larger than a depth dimension of the magnetostrictive sensor. In some embodiments, each well may have a length of about 1.1 mm, a width of about 0.3 mm, and a depth of about 70 µm.

In some embodiments, the system may further include a controller coupled to the sensor coil. The controller is configured to position the sensor coil beneath a first well of the index plate, apply a varying magnetic field, with the sensor coil, to a first magnetostrictive sensor within the first well, and detect a frequency response of the first magnetostrictive sensor with the sensor coil during application of the varying magnetic field. In some embodiments, the controller may be further configured to position the sensor coil beneath a second well of the index plate in response to detection of the frequency response of the first magnetostrictive sensor, apply a varying magnetic field, with the sensor coil, to a second magnetostrictive sensor within the second well, and detect a frequency response of the second magnetostrictive sensor with the sensor coil during application of the varying magnetic field. In some embodiments, the first magnetostrictive sensor may include a biorecognition element to bind with a microorganism, and the controller may be further configured to determine whether a microorganism is present based on the detected frequency response.

According to another aspect, a method for microorganism detection may include filling a basin with a liquid analyte, wherein the basin includes a index plate having an array of wells, wherein each well contains a magnetostrictive sensor that comprises magnetostrictive material, and wherein each well aligns the corresponding magnetostrictive sensor in a predetermined orientation; incubating the liquid analyte at a controlled temperature in response to filling the basin; positioning a sensor coil beneath a first well of the index plate; applying a varying magnetic field, using the sensor coil, to a first magnetostrictive sensor within the first well in response to incubating the liquid analyte, wherein the first magnetostrictive sensor comprises a biorecognition element to bind with a microorganism; detecting a frequency response of the first magnetostrictive sensor using the sensor coil while applying the varying magnetic field; and determining whether a microorganism is present based on the detected frequency response.

In some embodiments, the method may further include positioning the sensor coil beneath a second well of the index plate in response to detecting the frequency response of the first magnetostrictive sensor; applying a varying magnetic field, using the sensor coil, to a second magnetostrictive sensor within the second well; and detecting a frequency response of the second magnetostrictive sensor using the sensor coil while applying the varying magnetic field.

In some embodiments, positioning the sensor coil beneath the first well may include translating the basin to position the sensor coil beneath the first well. In some embodiments, positioning the sensor coil beneath the first well may include positioning an array of sensor coils that includes the sensor coil beneath the index plate of the basin, wherein each sensor coil of the array of sensor coils is positioned beneath a well of the array of wells.

In some embodiments, filling the basis with the liquid analyte may include flowing the liquid analyte continuously through the basin. In some embodiments, the analyte may comprise a liquid food product. In some embodiments, the analyte may comprise a liquid growth medium. In some embodiments, incubating the liquid analyte at the controlled temperature may include heating the liquid analyte with an infrared heating element. In some embodiments, incubating the liquid analyte may include incubating the liquid analyte at the controlled temperature for about 4 to 6 hours.

BRIEF DESCRIPTION OF THE DRAWINGS

The concepts described in the present disclosure are illustrated by way of example and not by way of limitation in the accompanying figures. For simplicity and clarity of illustration, elements illustrated in the figures are not necessarily drawn to scale. For example, the dimensions of some elements may be exaggerated relative to other elements for clarity. Further, where considered appropriate, reference labels have been repeated among the figures to indicate corresponding or analogous elements. The detailed description particularly refers to the accompanying figures in which.

DETAILED DESCRIPTION OF THE DRAWINGS

Figure 1:
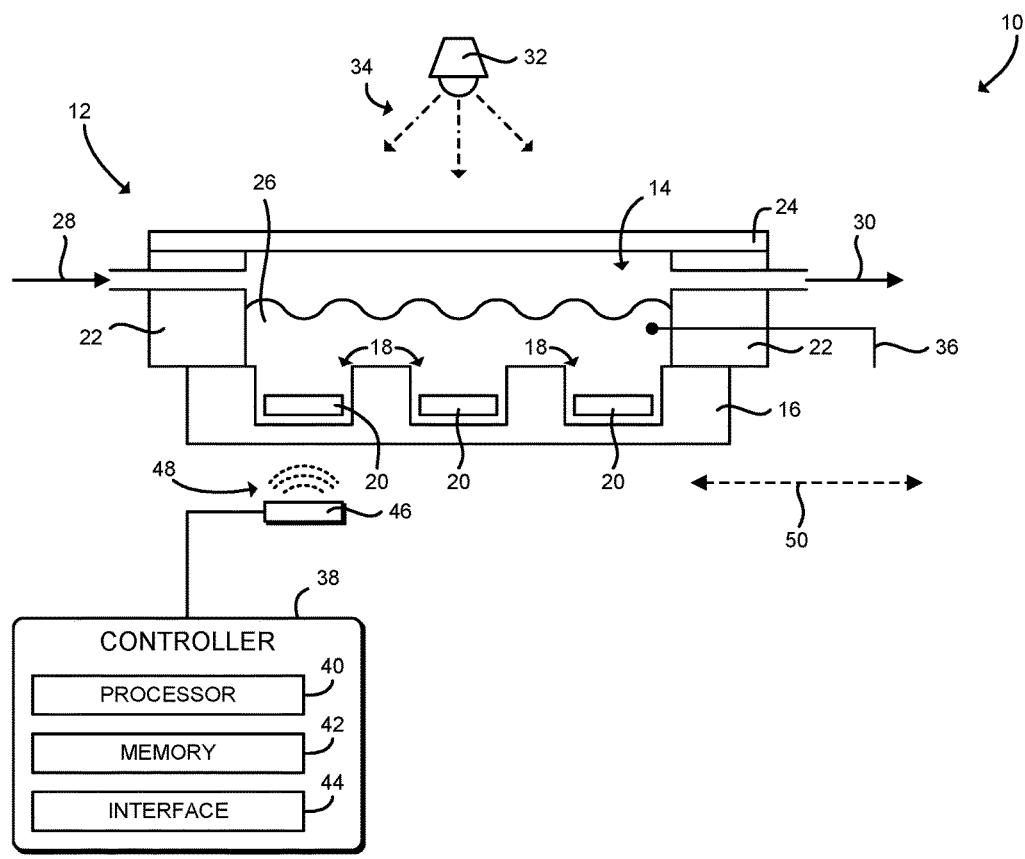
FIG. 1 is a cross-sectional diagram of a system for pathogen detection in a liquid analyte with magnetostrictive sensors.

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the present disclosure.

References in the specification to "one embodiment," "an embodiment," "an example embodiment," etcetera, indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to effect such feature, structure, or characteristic in connection with other embodiments whether or not explicitly described.

Figure 2:
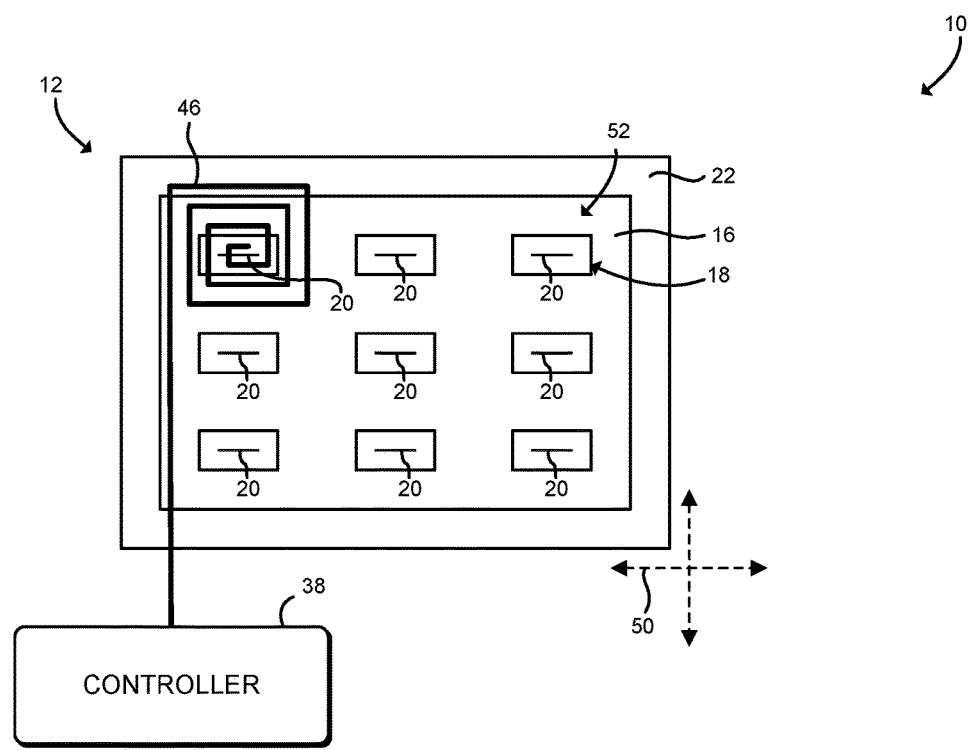
FIG. 2 is a top-view diagram of the system of FIG. 1.

Referring now to FIGS. 1 and 2, a simplified schematic diagram of one illustrative embodiment of a system 10 for pathogen detection in a liquid analyte with magnetostrictive sensors is shown. The system 10 includes a basin 12 that includes a culture chamber 14 that may be used to hold a liquid analyte 26 and multiple magnetostrictive sensors 20. In use, as described further below, the magnetostrictive sensors 20 may include a biorecognition element that binds to one or more microorganisms or other pathogens. The magnetostrictive sensors 20 may be exposed to a food product such as a liquid food (e.g., juice, milk, etc.). The basin 12 may be filled with a liquid analyte 26 such as a nutrient broth and allowed to incubate. After incubation, the magnetostrictive sensors 20 may be used to measure the presence and/or quantity of bound pathogens. Thus, the system 10 may be capable of accurately identifying whether a sample includes viable microorganisms. Additionally or alternatively, in some embodiments the system 10 may be used to detect other contaminants, such as chemical contaminants, metallic or magnetic particles, or other contaminant particles.

As described above, the system 10 includes a basin 12. The basin 12 defines a culture chamber 14 that is surrounded by an index plate 16, a surrounding wall 22, and a transparent cover 24. The components of the basin 12 may be bonded together using glue or another bonding agent. The index plate 16 is positioned at the bottom of the basin 12 and includes multiple wells 18 that open into the culture chamber 14 of the basin 12. The wells 18 may be arranged on the index plate 16 in a rectangular array 52, as best shown in FIG. 2. In some embodiments, the index plate 16 may be embodied as polyethylene terephthalate glycol-modified (PETG) or another suitable thermoplastic. The wells 18 may be formed in the index plate 16 using photolithography combined with a vacuum forming process. As best shown in FIG. 2, each of the wells 18 has a rectangular opening into the culture chamber 14 of the basin 12. Each of the wells 18 is sized to receive a magnetostrictive sensor 20. Because the magnetostrictive sensors 20 are also rectangular, the wells 18 hold the magnetostrictive sensors 20 in a predetermined orientation, which may improve wireless detection of microorganisms or other pathogens, as described further below.

The magnetostrictive sensors 20 are small devices made of a magnetostrictive and/or magnetoelastic material that may be coated with a biorecognition element that binds to a particular target particle, such as a pathogen. For example, the biorecognition element may include antibodies or genetically engineered phages that bind to particular bacteria, such as *Salmonella Typhimurium*. The magnetostrictive material converts magnetic energy to mechanical energy and vice versa. In other words, magnetostrictive materials generate mechanical strain when the magnetic energy is applied and generate magnetic energy in response to mechanical strain. Throughout this disclosure, the terms magnetostrictive material and magnetoelastic material may be used interchangeably. In the illustrative embodiment, the magnetostrictive sensors 20 are embodied as thin strips of material that may be actuated into resonance by application of a varying magnetic field 48. The magnetostrictive sensors 20 are illustratively rectangular in shape; however, in other embodiments, any elongated shape may be used. Upon contact with the specific target pathogen, the pathogen binds with the biorecognition element and increases the mass of the magnetostrictive sensor 20. This additional mass causes the characteristic frequency of the magnetostrictive sensors 20 to decrease. As described further below, the characteristic frequency may be measured by a sensor coil 46, allowing quantitative detection and characterization of the pathogen. One embodiment of a magnetostrictive sensor 20 is further described below in connection with FIGS. 3-4.

As shown in FIGS. 1-2, the surrounding wall 22 is attached to the top of the index plate 16 and surrounds the array 52 of wells 18. The surrounding wall 22 may be embodied as polydimethylsiloxane (PDMS) or another suitable silicone material. The index plate 16 and the surrounding wall 22 are watertight, allowing the basin 12 to be filled with a liquid analyte 26. The analyte 26 may be embodied as a liquid growth medium such as a nutrient broth. Additionally or alternatively, in some embodiments the analyte 26 may be embodied as a liquid food product (e.g., juice or milk), water, process water, blood or other bodily fluids, oil or air, and/or soaking water. As shown, the basin 12 includes an inlet port 28 and an outlet port 30 which may be used to flow the analyte 26 into the basin. As described further below, the analyte 26 may be injected into the basin 12 in a single injection, in a continuous flow, or in a combination of sequences for detection of microorganisms or other pathogens.

The transparent cover 24 is attached to the top of the surrounding wall 22 and covers the interior of the basin 12. The transparent cover 24 may be embodied as a material such as glass that is transparent to infrared light. An infrared heating element 32 may be positioned to shine infrared radiation 34 through the transparent cover 24 into the basin 12. The infrared heating element 32 may be used to maintain the analyte 26 at a controlled temperature, such as 37° Celsius. The basin 12 may include a temperature sensor 36, such as a thermocouple, that extends into the analyte 26 and may be used to control the temperature of the analyte 26.

The system 10 also includes a controller 38 coupled to a sensor coil 46. The sensor coil 46 may be positioned beneath one or more of the wells 18 of the index plate 16. The sensor coil 46 and/or the index plate 16 may be translatable to position the sensor coil beneath a particular well 18, as shown by the arrows 50 of FIGS. 1 and 2. As described further below, the controller 38 causes the sensor coil 46 to apply a varying magnetic field 48 to the magnetostrictive sensors 20. The controller 38 measures a magnetic field produced by the magnetostrictive sensors 20 in response to the varying magnetic field 48 using the sensor coil 46. The controller 38 determines a frequency response of the magnetostrictive sensors 20 based on the measured magnetic field. This frequency response is related to the resonant frequency of the magnetostrictive sensors 20, as well as other material properties (e.g., the magnetoelastic coupling coefficient) and the environment (e.g., friction forces or damping effects). As described further below, microorganisms or other pathogens bound to the magnetostrictive sensors 20 may cause an increase in the mass of the magnetostrictive sensors 20 and a corresponding decrease in the frequency response. The system 10 may determine whether microorganisms or other pathogens are present by determining whether the frequency response shifts. Multiple types of pathogens may be detected simultaneously by using separate groups of magnetostrictive sensors 20, with each group of magnetostrictive sensors 20 binding to a different type of microorganism or other pathogen. Additionally, although illustrated in FIG. 2 as positioning the sensor coil 46 beneath a single well 18, it should be understood that the sensor coil 46 may be positioned beneath multiple wells 18 and/or magnetostrictive sensors 20. For example, in some embodiment, the sensor coil 46 may be embodied as an asymmetric flat coil that extends beneath multiple wells 18.

As described briefly above, the system 10 includes the controller 38. The controller 38 is responsible for activating or energizing electronically-controlled components of the system 10, including the sensor coil 46. The controller 38 is also responsible for interpreting electrical signals received from components of the system 10, including the sensor coil 46. To do so, the controller 38 may include a number of electronic components commonly associated with units utilized in the control of electronic and electromechanical systems. For example, the controller 38 may include, amongst other components customarily included in such devices, a processor 40 and a memory device 42. The processor 40 may be any type of device capable of executing software or firmware, such as a microcontroller, microprocessor, digital signal processor, or the like. The memory device 42 may be embodied as one or more non-transitory, machine-readable media. The memory device 42 is provided to store, amongst other things, instructions in the form of, for example, a software routine (or routines) which, when executed by the processor 40, allows the controller 38 to perform sensor interrogation and pathogen detection using the other components of the system 10.

The controller 38 also includes an analog interface circuit 44, which may be embodied as any electrical circuit(s), component, or collection of components capable of performing the functions described herein. The analog interface circuit 44 converts output signals (e.g., from the sensor coil 46) into signals which are suitable for presentation to an input of the processor 40. In particular, the analog interface circuit 44, by use of a network analyzer, an analog-to-digital (A/D) converter, or the like, converts analog signals into digital signals for use by the processor 40. Similarly, the analog interface circuit 44 converts signals from the processor 40 into output signals which are suitable for presentation to the electrically-controlled components associated with system 10 (e.g., the sensor coil 46). In particular, the analog interface circuit 44, by use of a variable-frequency signal generator, digital-to-analog (D/A) converter, or the like, converts digital signals generated by the processor 40 into analog signals for use by the electronically-controlled components associated with the system 10. It is contemplated that, in some embodiments, the analog interface circuit 44 (or portions thereof) may be integrated into the processor 40.

As also mentioned above, the controller 38 is coupled to the sensor coil 46. In the illustrative embodiment, the sensor coil 46 is used as an energizing excitation source for the magnetostrictive sensors 20 and as a detector of signals received from the magnetostrictive sensors 20. In some embodiments, the sensor coil 46 may be a solenoid with loops having a generally rectangular cross-section. In some embodiments, the sensor coil 46 may be embodied as a flat coil as described in U.S. Patent Publication No. 2014/0120524 ("In-Situ Pathogen Detection Using Magnetoelastic Sensors"), the entire disclosure of which is incorporated herein by reference. To improve performance of the system 10, the sensor coil 46 may be impedance-matched to the electrical circuitry of the controller 38. Additionally, although illustrated as a single sensor coil 46, it should be understood that in some embodiments the system 10 may include a separate drive coil and one or more pickup coils to perform the functions of the sensor coil 46.

The system 10 may further include a magnetic field generator configured to generate a constant, uniform magnetic field. The uniform magnetic field extends through the analysis wells 18. The uniform magnetic field may bias the magnetostrictive sensors 20 during application of the varying magnetic field 48, increasing the magnitude of the frequency response. The magnetic field generator may be embodied as any component capable of generating the uniform magnetic field, for example, a pair of permanent magnet arrays or a Helmholtz coil.

Figure 3:
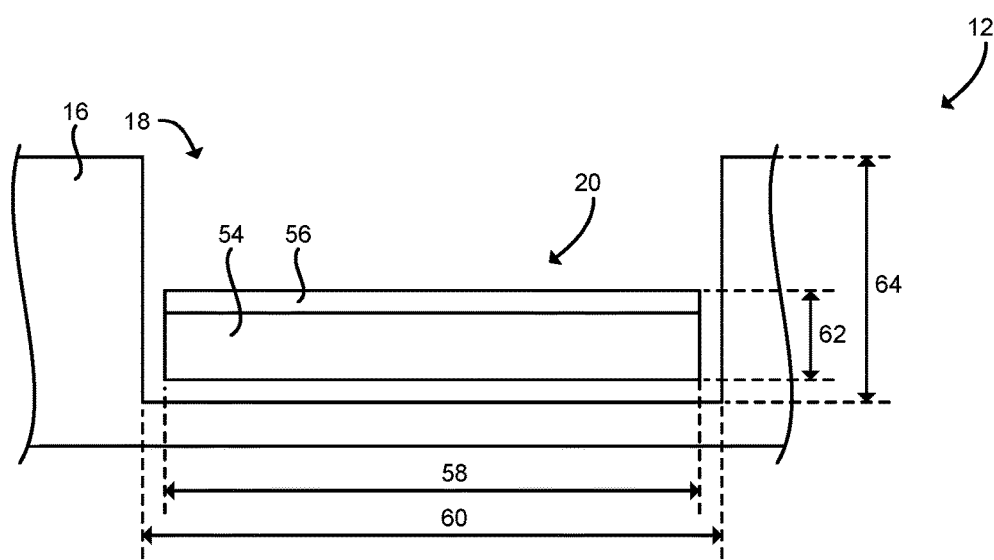
FIG. 3 is a cross-sectional diagram of well that includes a magnetostrictive sensor of the system of FIGS. 1-2.
Figure 4:
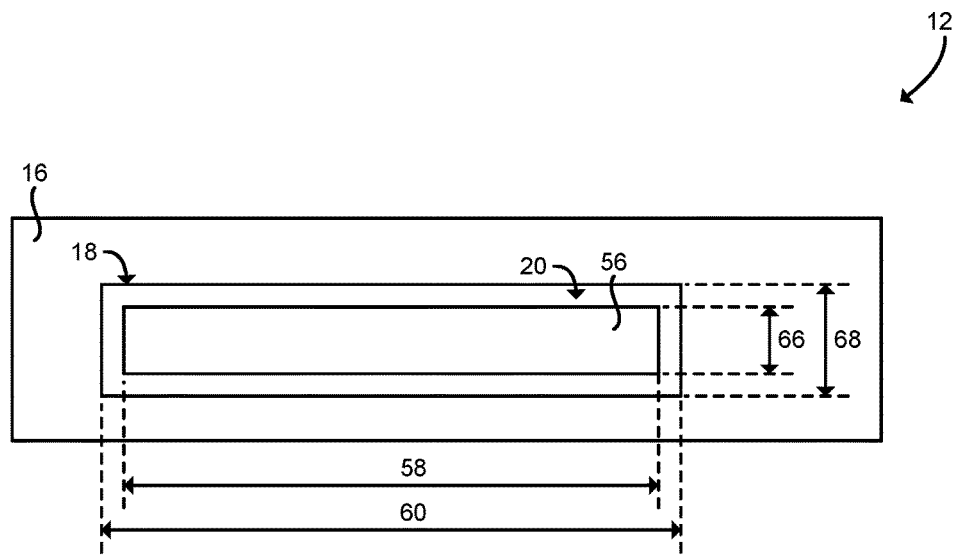
FIG. 4 is a top-view diagram of the well that includes a magnetostrictive sensor of the system of FIGS. 1-3.

Referring now to FIGS. 3 and 4, an illustrative part of the basin 12 including a well 18 formed in the index plate 16 is shown. As shown, the well 18 includes a magnetostrictive sensor 20. The sensor 20 includes a body 54 coated with an immobilized biorecognition element 56. The body 54 is made from a magnetoelastic material, such as a magnetostrictive alloy. In one illustrative embodiment, the body 54 may be mechanically polished and cut (diced) from a strip of METGLAS™ 2826 MB, which is commercially available from Honeywell Inc., of Conway, S.C. Additionally, although illustrated as including a single side of the body 54 coated with the biorecognition element 56, it should be understood that in some embodiments two or more sides of the body 54 may be coated with the biorecognition element 56. Additionally or alternatively, in some embodiments, some or all of the sensors 20 may not include a biorecognition element 56. For example, some of the sensors 20 may be used as control sensors, or the sensors 20 may be used to detect metallic or other magnetic particles.

In the illustrative embodiment, each magnetostrictive sensor 20 has a length 58, a thickness 62 (shown in FIG. 3), and a width 66 (shown in FIG. 4). For example, in some embodiments the magnetostrictive sensors 20 may be one millimeter in length, four millimeters in length, or another length. The magnetostrictive sensor 20 is in the shape of a thin strip, meaning that the length 58 is larger than the width 66 and much larger than the thickness 62 (i.e., L>w>>t). Upon application of a varying magnetic field, the dimensions of the magnetostrictive sensor 20 change. Accordingly, the magnetostrictive sensor 20 mechanically vibrates in response to the varying magnetic field. In particular, due to its thin strip shape, the magnetostrictive sensor 20 vibrates mainly longitudinally; in other words, when an oscillating external magnetic field is applied, the magnetostrictive sensor 20 vibrates between a length L and a length L'. The fundamental resonant frequency $f_0$ of this longitudinal oscillation is given as:

$$f_0 = \frac{V}{2L}, \quad (1)$$

where V is the acoustic velocity of the material along its length L. Addition of a small mass ($\Delta m \ll M$) on the magnetostrictive sensor 20 surface causes a change in the resonant frequency ($\Delta f$). This resonant frequency change is proportional to the initial frequency $f_0$ and the mass added ($\Delta m$) and is inversely proportional to the initial sensor mass M. Assuming the added mass is uniformly distributed on the surface of the magnetostrictive sensor 20, the resonant frequency change may be approximated as:

$$\Delta f = -\frac{f_0 \Delta m}{2M} (\Delta m \ll M). \quad (2)$$

The negative sign in Equation (2) means that the resonant frequency of the magnetostrictive sensor 20 decreases with the increase of the mass load. The additional mass load on the magnetostrictive sensor 20 can be obtained by measuring the shift in the resonant frequency (or another characteristic frequency related to the resonant frequency).

When the magnetostrictive sensor 20 comes into contact with a target pathogen, the biorecognition element 56 immobilized on the magnetostrictive sensor 20 surface will bind/capture the target pathogen. This adds an additional mass load on the magnetostrictive sensor 20. As described above, this additional mass causes a drop in a characteristic frequency of the magnetostrictive sensor 20. Therefore, the presence of any target pathogens can be identified by monitoring for a shift in the characteristic frequency of the magnetostrictive sensor 20. Additionally or alternatively, rather than a biorecognition element 56, the magnetostrictive sensor 20 may include a chemical layer that similarly binds with one or more contaminants such as mercury, heavy metals, or other chemicals and/or contaminants.

The simple strip-shaped configuration of the illustrative magnetostrictive sensor 20 described above may make fabrication relatively easy and/or inexpensive. Additionally, the magnetostrictive sensors 20 are passive sensors that do not require on-board power. As described above, the magnetostrictive sensor 20 may be fabricated by mechanical methods (e.g., polish and dice) or by microelectronics fabrication methods (e.g., sputter deposit, thermal deposit, or electrochemical deposit). These methods can mass-produce fabricated magnetostrictive sensors 20 with very low cost. Additional details of illustrative magnetoelastic ligand detectors are described in U.S. Pat. No. 7,759,134 ("Magnetostrictive Ligand Sensor"), the entire disclosure of which is incorporated herein by reference.

As described above, the biorecognition element 56 may be immobilized on the surface of each magnetostrictive sensor 20 to bind a specific target pathogen. In some embodiments, the biorecognition element 56 may be embodied as a chemical binding element or an interaction layer immobilized on the body 54 of the magnetostrictive sensor 20. For example, the biorecognition element 56 may be a traditional antibody. Additionally or alternatively, in some embodiments, the biorecognition element 56 may be a genetically engineered bacteriophage ("phage"). The use of phages as a substitute for antibodies offers a stable, reproducible, and inexpensive alternative. In particular, phages have high affinity for binding with target pathogen cells, the phage structure is robust and stable, and phages may bind target pathogens in air with certain humidity. Additionally or alternatively, the biorecognition element 56 may be embodied as DNA, RNA, proteins, aptamers, or other biorecognition elements. Specific ligand recognition devices that may be illustratively used as the biorecognition element 56, as well as illustrative application methods, are discussed in U.S. Pat. No. 7,138,238 ("Ligand Sensor Devices and Uses Thereof"), U.S. Pat. No. 7,267,993 ("Phage Ligand Sensor Devices and Uses Thereof"), and U.S. Pat. No. 7,670,765 ("Method of Forming Monolayers of Phage-Derived Products and Used Thereof"), the entire disclosures of which are incorporated herein by reference.

As shown in FIGS. 3 and 4, the well 18 has dimensions that are larger than the sensor 20, to allow the well 18 to receive the sensor 20. In particular, the well has a length 60, a depth 64 (shown in FIG. 3), and a width 68 (shown in FIG. 4). The length 60 and the width 68 may be slightly larger than the corresponding length 58 and width 66 of the sensor 20. For example, each of the length 60 and the width 68 may be between 1.00001% and 1.2% larger than respective length 58 and width 66 of the sensor 20. By being slightly larger than the sensor 20, the well 18 may cause the sensor 20 to align in a predetermined direction, which may improve the sensitivity, signal-to-noise ratio, or other operating characteristics of the magnetostrictive sensors 20 and thereby improve accuracy of the system 10. As shown in FIG. 3, the depth 64 is larger than the thickness 62 of the sensor 20. For example, the depth 64 may be between 1 and 10,000 times larger than the thickness of the sensor 20. In an illustrative embodiment, the length 60 may be 1.1 mm, the width 68 may be 0.3 mm, and the depth 64 may be 70 µm.

Figure 5:
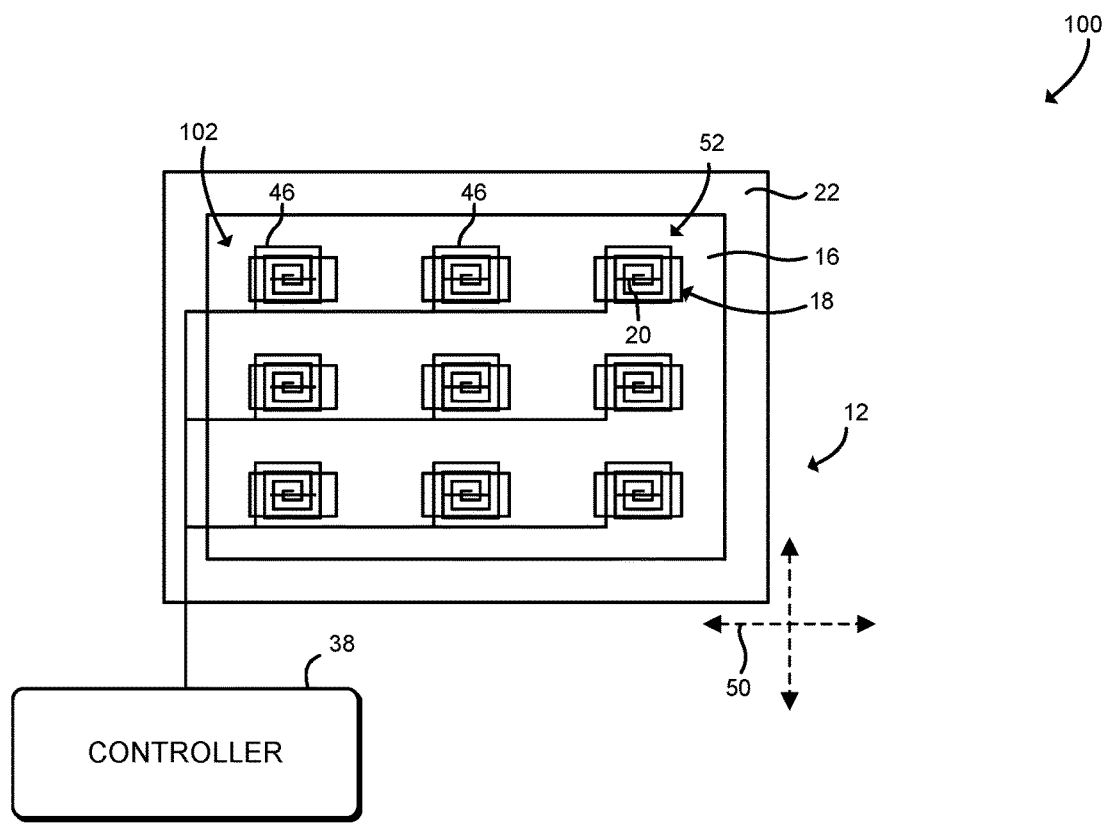
FIG. 5 is a top-view diagram of a system for pathogen detection in a liquid analyte with magnetostrictive sensors.

Referring now to FIG. 5, another illustrative embodiment of a system 100 for pathogen detection in a liquid analyte with magnetostrictive sensors is shown. Similar to the system 10 of FIGS. 1-4, the system 100 includes a basin 12 having an index plate 16 that includes an array 52 of wells 18 to receive magnetostrictive sensors 20. As shown in FIG. 5, a controller 38 may be coupled to an array 102 of sensor coils 46. The array 102 of sensor coils 46 may be positioned so that each sensor coil 46 is below a well 18. As described further below, the array 102 of sensor coils 46 may be used to simultaneously and/or sequentially measure multiple magnetostrictive sensors 20 in multiple wells 18. Additionally or alternatively, although illustrated as including a sensor coil 46 for each well 18, in some embodiments, system 100 may include a different number of sensor coils 46 and wells 18, and the basin 12 and/or array 102 may be translatable to position the array 102 beneath particular wells 18, as shown by the arrows 50.

Figure 6:
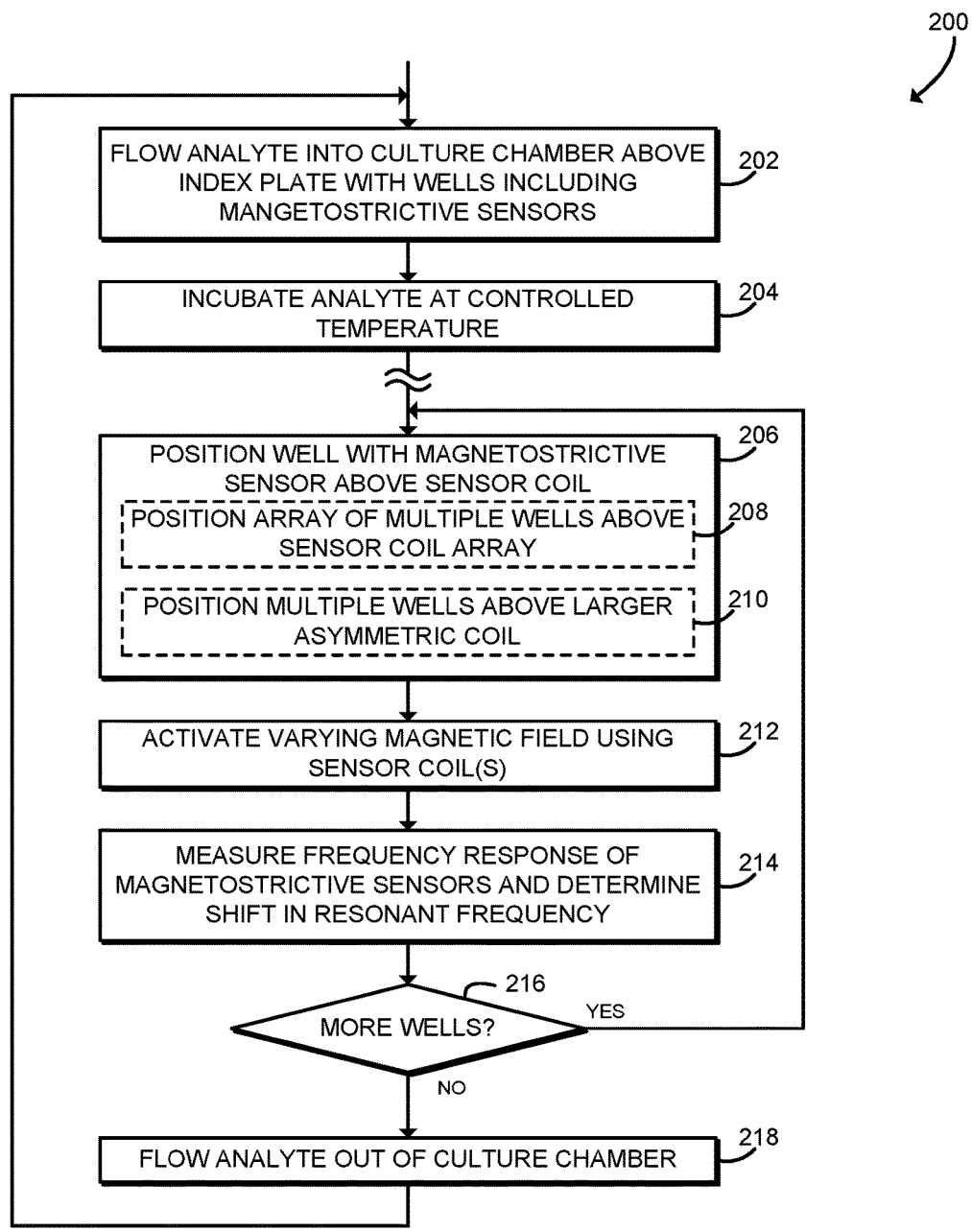
FIG. 6 is a simplified flow diagram of one embodiment of a method for pathogen detection that may be performed using the system of FIGS. 1-5.

Referring now to FIG. 6, one illustrative embodiment of a method 200 that may be used for pathogen or other contaminant detection with a system 10, 100 is shown as a simplified flow diagram. The method 200 is illustrated as a series of blocks 202-218, some of which may be optionally performed in some embodiments (and, thus, are shown in dashed lines). It will be appreciated by those of skill in the art that some embodiments of the method 200 may include additional or different processes and sub-processes.

The method 200 begins with block 202, in which analyte 26 is flowed into the culture chamber 14 of the basin 12. As described above, the basin 12 includes an index plate 16 at its bottom that includes multiple wells 18. Each of the wells 18 includes a magnetostrictive sensor 20. In some embodiments, the sensors 20 may have previously been exposed to a sample that is to be tested for contamination before the analyte 26 is flowed into the culture chamber 14. For example, the sensors 20 may have previously been in physical contact with a food product such as fresh vegetables or a liquid food product such as juice or milk. Additionally or alternatively, the analyte 26 may be a liquid food product that is to be tested. Illustratively, each of the magnetostrictive sensors 20 includes a biorecognition element 56 to bind to a particular microorganism. However, it should be understood that in some embodiments the magnetostrictive sensors 20 may bind to any targeted organism, chemical contaminants, metallic or magnetic particles, or other contaminant particles. In some embodiments, some of the magnetostrictive sensors 20 may include different biorecognition elements to target different contaminant particles (e.g., targeting multiple pathogens). Additionally, in some embodiments, the magnetostrictive sensors 20 may bind to metallic particles or other magnetic particles using magnetic effects, rather than a biorecognition element.

As described above, the analyte 26 may be embodied as a liquid growth medium such as a nutrient broth. Additionally or alternatively, the analyte 26 may be embodied as a liquid food product (e.g., milk, juice, or other food product). The analyte 26 may be injected into the culture chamber 14 in a single injection, in a continuous flow, or in a combination of sequences for detection of microorganisms or other pathogens. The analyte 26 may be pumped into the culture chamber 14 using the inlet port 28.

In block 204, the analyte 26 is incubated at a controlled temperature, such as 37° Celsius. The infrared heating element 32 may be used to heat the analyte 26, and the temperature of the analyte 26 may be measured with the temperature sensor 36. A controller (e.g., the controller 38) may use the temperature sensor 36 and the infrared heating element 32 to maintain the analyte 26 at the controlled temperature. The analyte 26 may be allowed to remain at the controlled temperature for a long enough time to allow any viable microorganisms bound to magnetostrictive sensors 20 to reproduce. For example, the analyte 26 may be allowed to incubate for 4-6 hours.

After incubation, in block 206 a well 18 that includes a magnetostrictive sensor 20 is positioned above the sensor coil 46. The well 18 may be positioned by translating the basin 12 and/or the sensor coil 46. For example, in some embodiments, the controller 38 may control a two-dimensional translation stage or other actuator(s) to move a well 18 of the index plate 16 above the sensor coil 46. Although illustrated as being positioned above the sensor coil 46, it should be understood that in other embodiments the well 18 may be otherwise positioned in proximity to the sensor coil 46. In some embodiments, in block 208 the array 52 of multiple wells 18 may be positioned above an array 102 of sensor coils 46, as shown in FIG. 5. In those embodiments, each well 18 may be positioned above a corresponding sensor coil 46. In some embodiments, in block 210, multiple wells 18 may be positioned above a single, larger sensor coil 46, such as an asymmetric flat coil.

In block 212, the sensor coil 46 is activated to generate the varying magnetic field 48. As described above, the varying magnetic field 48 causes the magnetostrictive sensors 20 to oscillate. Because each well 18 aligns the magnetostrictive sensor 20 in a predetermined orientation, the longitudinal oscillation of all (or, at least, most) of the sensors 20 may be in the same direction. Thus, the magnetic flux picked up by the sensor coil 46 may thus contain frequency response information for all (or, at least, most) of the sensors 20. The frequency of the varying magnetic field 48 may be varied through a range of frequencies. The range of frequencies may include a resonant frequency of the magnetostrictive sensors 20 when a microorganism has not been bound (i.e., when the sensors 20 are unloaded). For example, in some embodiments the range of frequencies applied by the sensor coil 46 may cover from 50% of unloaded resonant frequency to slightly more than the unloaded resonant frequency. Binding of microorganisms on the magnetostrictive sensor 20 surface is typically a small mass change, and the decrease in the characteristic frequency of the magnetostrictive sensors 20 due to this small mass change is normally less than 50% of the unloaded resonant frequency of the magnetostrictive sensor 20.

In block 214, the frequency response of the magnetostrictive sensors 20 is measured using the sensor coil 46, and any shift in resonant frequency of the magnetostrictive sensors 20 is determined. The controller 38 may monitor the characteristic frequency in real time or record data for later analysis. The measurement of each magnetostrictive sensor 20 may require about 2 seconds. As described above, the magnetostrictive sensors 20 include the biorecognition element 56 that will bind with microorganisms upon contact.

Binding increases the mass of the magnetostrictive sensor 20, which causes a resonant frequency of the magnetostrictive sensor 20 to decrease. Thus, a measured shift in the resonant frequency indicates that microorganisms are present on the magnetostrictive sensor 20. In some embodiments, the shift in resonant frequency may be determined by comparing the frequency response of the magnetostrictive sensors 20 to the frequency response of one or more control sensors that do not include a biorecognitition element. In some embodiments, measurement of the resonant frequency of the magnetostrictive sensors 20 may be repeated over time, for example before and after incubation as described above in connection with block 204. A shift in resonant frequency after incubation may indicate that the microorganisms bound to the magnetostrictive sensors 20 are reproducing and are therefore viable. In some embodiments, the shift in resonant frequency may be used to determine both the identify of detected pathogens and the quantity of detected pathogens.

In block 216, it is determined whether additional wells 18 should be measured. For example, the controller 38 may determine whether additional analysis wells 18 remain in a pre-programmed pattern of wells 18 in the index plate 16. Of course, as described above, in some embodiments all of the wells 18 may be measured simultaneously, for example using an array 102 of sensor coils 46. If additional analysis wells 18 should be measured, the method 200 loops back to block 206, in which the sensor coil 46 may be positioned beneath additional wells 18. If no further analysis wells 18 remain to be measured, the method 200 advances to block 218.

In block 218, the analyte 26 flows out of the culture chamber 14. As described above, the analyte 26 may be analyzed in a single injection, in a continuous flow, or in another combination of sequences. Thus, the analyte 26 may flow out of the culture chamber 14 through the outlet port 30. After flowing the analyte 26 out of the culture chamber 14, the method 200 loops back to block 202 to perform additional measurements.

While certain illustrative embodiments have been described in detail in the figures and the foregoing description, such an illustration and description is to be considered as exemplary and not restrictive in character, it being understood that only illustrative embodiments have been shown and described and that all changes and modifications that come within the spirit of the disclosure are desired to be protected. There are a plurality of advantages of the present disclosure arising from the various features of the apparatus, systems, and methods described herein. It will be noted that alternative embodiments of the apparatus, systems, and methods of the present disclosure may not include all of the features described yet still benefit from at least some of the advantages of such features. Those of ordinary skill in the art may readily devise their own implementations of the apparatus, systems, and methods that incorporate one or more of the features of the present disclosure.

The invention claimed is:

1. A method for microorganism detection, the method comprising:
   filling a basin with a liquid analyte, wherein the basin includes a index plate having an array of wells, wherein each well contains a magnetostrictive sensor that comprises magnetostrictive material, and wherein each well aligns the corresponding magnetostrictive sensor in a predetermined orientation;
   incubating the liquid analyte at a controlled temperature in response to filling the basin;
   positioning a sensor coil beneath a first well of the index plate;
   applying a varying magnetic field, using the sensor coil, to a first magnetostrictive sensor within the first well in response to incubating the liquid analyte, wherein the first magnetostrictive sensor comprises a biorecognition element to bind with a microorganism;
   detecting a frequency response of the first magnetostrictive sensor using the sensor coil while applying the varying magnetic field; and
   determining whether a microorganism is present based on the detected frequency response.

2. The method of claim 1, wherein positioning the sensor coil beneath the first well comprises translating the basin to position the sensor coil beneath the first well.

3. The method of claim 1, wherein incubating the liquid analyte comprises incubating the liquid analyte at the controlled temperature for about 4 to 6 hours.

4. The method of claim 1, further comprising:
   positioning the sensor coil beneath a second well of the index plate in response to detecting the frequency response of the first magnetostrictive sensor;
   applying a varying magnetic field, using the sensor coil, to a second magnetostrictive sensor within the second well; and
   detecting a frequency response of the second magnetostrictive sensor using the sensor coil while applying the varying magnetic field.

5. The method of claim 1, wherein filling the basin with the liquid analyte comprises flowing the liquid analyte continuously through the basin.

6. The method of claim 1, wherein the analyte comprises a liquid food product.

7. The method of claim 1, wherein the analyte comprises a liquid growth medium.

8. The method of claim 1, wherein determining whether a microorganism is present based on the detected frequency response comprises comparing the frequency response of the first magnetostrictive sensor to a frequency response of a control magnetostrictive sensor, wherein the control magnetostrictive sensor does not include a biorecognition element to bind with a microorganism.

9. The method of claim 1, further comprising:
   detecting an initial frequency response of the first magnetostrictive sensor using the sensor coil while applying the varying magnetic field, in response to filling the basin with the liquid analyte and prior to incubating the liquid analyte;
   wherein incubating the liquid analyte comprises incubating the liquid analyte in response to detecting the initial frequency response; and
   wherein determining whether a microorganism is present comprises comparing the frequency response of the first magnetostrictive sensor to the initial frequency response.

10. The method of claim 1, wherein incubating the liquid analyte at the controlled temperature comprises heating the liquid analyte with an infrared heating element.

* * * * *